United States Patent [19]

Ozawa et al.

[11] 4,407,813
[45] Oct. 4, 1983

[54] INSECTICIDAL PYRAZOLINE DERIVATIVES AND COMPOSITION

[75] Inventors: Kiyomi Ozawa; Yasuyuki Nakajima; Makoto Tsugeno; Shigeru Ishii; Masataka Hatanaka, all of Funabashi, Japan

[73] Assignee: Nissan Chemical Industries Ltd., Tokyo, Japan

[21] Appl. No.: 292,710

[22] Filed: Aug. 13, 1981

[30] Foreign Application Priority Data

Feb. 17, 1981 [JP] Japan .................................. 56-21767
Jun. 19, 1981 [JP] Japan .................................. 56-94850

[51] Int. Cl.$^3$ .................... A01N 43/56; C07D 231/06
[52] U.S. Cl. ................................. 424/273 P; 548/379
[58] Field of Search ..................... 548/379; 424/273 P

[56] References Cited

U.S. PATENT DOCUMENTS 3,991,073 11/1976 Mulder et al. ........................ 424/263
4,010,271 3/1977 Mulder et al. .................... 424/273 P
4,070,365 1/1978 van Daalen et al. ................ 548/379
4,095,026 6/1978 Mulder et al. ....................... 548/379
4,140,787 2/1979 Sirrenberg et al. .
4,140,792 2/1979 Sirrenberg et al. ................. 548/379
4,156,007 5/1979 van Daalen et al. ............ 424/273 P
4,174,393 11/1979 van Daalen et al. .

OTHER PUBLICATIONS

Wellinga et al., "1-Phenylcarbamoyl-2-Pyrazolines: a New Class of Insecticides. 1. Synthesis & Insecticidal Properties of 3-Phenyl-1-phenylcarbamoyl-2-pyrazolines," *Journal of Agric. Food Chem.*, vol. 25, No. 5, pp. 987–992, 1977.

Van Hes et al., "1-Phenylcarbamoyl-2-Pyrazolines: A New Class of Insecticides. 2. Synthesis and Insecticidal Properties of 3,5-Diphenyl-1-phenylcarbamoyl-2-pyrazolines," *Journal of Agric. Food Chem.*, vol. 26, No. 4. pp. 915–918, 1978.

Grosscurt et al., "1-Phenylcarbamoyl-2-pyrazolines, A New Class of Insecticides. 3. Synthesis and Insecticidal Properties of 3,4–Diphenyl-1-Phenylcarbamoyl-2-Pyrazolines,"*Journal of Agric. Food Chem.*, vol. 27, No. 2, pp. 406–409, 1979.

*Primary Examiner*—Henry R. Jiles
*Assistant Examiner*—Natalia Harkaway
*Attorney, Agent, or Firm*—Oblon, Fisher, Spivak, McClelland & Maier

[57] ABSTRACT

Pyrazoline derivatives having the formula

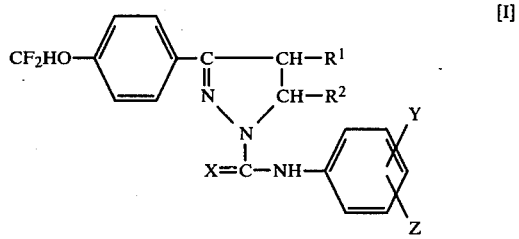

wherein $R^1$ represents hydrogen atom, a lower alkyl group, phenyl group or a halogen-substituted phenyl group; $R^2$ represents hydrogen atom or phenyl group which can have halogen substituents; X represents oxygen or sulfur atom; Y and Z respectively represent hydrogen atom, a halogen atom, a lower alkyl group, a lower alkoxy group, nitro-group, trifluoromethyl group, a lower alkylthio group, an acyl group, nitrile group or a lower alkyl sulfonyl group.

17 Claims, No Drawings

INSECTICIDAL PYRAZOLINE DERIVATIVES AND COMPOSITION

BACKGROUND OF THE INVENTION

1. Field of the Invention

The present invention relates to novel pyrazoline derivatives a production thereof and an insect pesticide containing a pyrazoline derivative thereof as an active ingredient.

2. Description of the Prior Art

Various chemicals for insect pesticides have been studied and developed for a long time. These insect pesticides have been contributed for improvement of a productivity of agricultural crops. However, a development of a novel chemical having superior insect pesticidal activity has been required.

It has been known that 1-carbamoyl-2-pyrazoline derivatives are effective as insect pesticides in Japanese Unexamined Patent Publication No. 87028/1973, No. 413581/1976 and No. 87166/1977, etc. as pyrazoline derivatives.

SUMMARY OF THE INVENTION

It is an object of the present invention to provide novel insect pesticidal compounds which have excellent effects and low toxicity to mammals and fishes.

It is another object of the present invention to provide a process for producing novel pyrazoline derivatives.

The foregoing and other objects of the present invention have been attained by providing pyrazoline derivatives having the formula

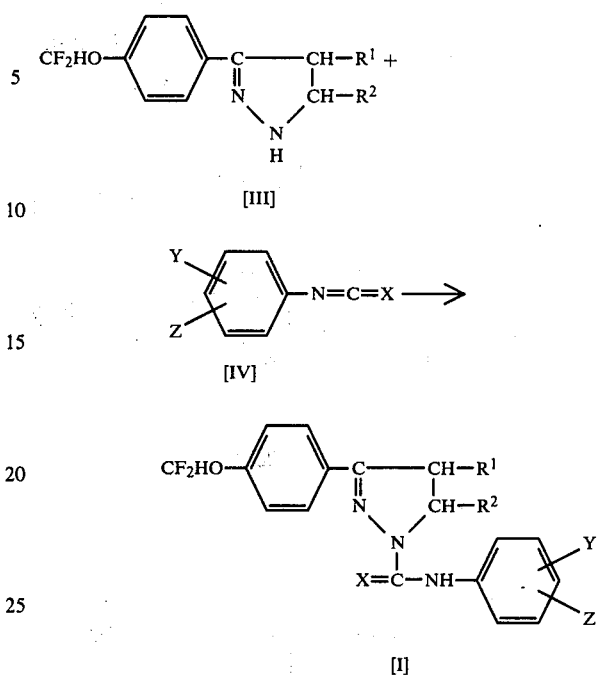

wherein $R^1$ represents hydrogen atom, a lower alkyl group, phenyl group or a halogen-substituted phenyl group; $R^2$ represents hydrogen atom or phenyl group which can have halogen substituents; X represents oxygen or sulphur atom; Y and Z respectively represent hydrogen atom, a halogen atom, a lower alkyl group, a lower alkoxy group, nitro group, trifluoromethyl group, a lower alkylthio group, an acyl group, nitrile group or a lower alkyl sulfonyl group.

DETAILED DESCRIPTION OF THE PREFERRED EMBODIMENTS

The compounds of the present invention have been produced by the following reaction scheme:

wherein $R^1$ represents hydrogen atom, a lower alkyl group, phenyl group or a halogen-substituted phenyl group; $R^2$ represents hydrogen atom or phenyl group which can have halogen substituents; X represents oxygen or sulfur atom; Y and Z respectively represent hydrogen atom, a halogen atom, a lower alkyl group, a lower alkoxy group, nitro group, trifluoromethyl group, a lower alkylthio group, an acyl group, nitrile group or a lower alkyl sulfonyl group.

The pyrazoline derivatives can be produced by reacting 3-(4-difluoromethoxyphenyl)-2-pyrazoline derivative having the formula (III) with phenylisocyanate or phenylisothiocyanate having the formula (IV) in the presence or absence of an inert solvent.

Suitable inert solvents include ethyl ether, benzene, toluene, acetonitrile, pyridine, dichloromethane, chloroform and carbon tetrachloride.

The reaction temperature and the reaction time can be selected depending upon the starting material. Usually, the reaction temperature is in a range of −20° C. to 100° C. The reaction time is preferably in a range of 0.5 to 24 hours.

The 3-(4-difluoromethoxyphenyl) 2-pyrazoline derivatives having the formula (III) as the starting material used in the reaction scheme are also novel compounds which can be usually produced by the following reaction schemes.

Scheme 1

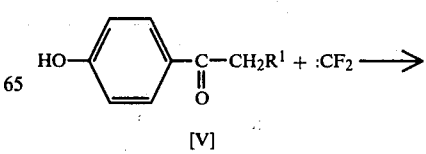

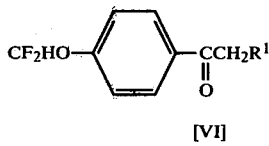

[VI]

wherein $R^1$ represents hydrogen atom, a lower alkyl group, or phenyl group or halogen-substituted phenyl group.

Scheme (2-A)

The compound having the formula (III) wherein $R^1$ represents phenyl group or halogen-substituted phenyl group and $R^2$ represents hydrogen atom;

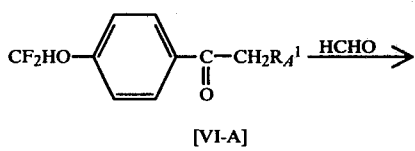

[VI-A]

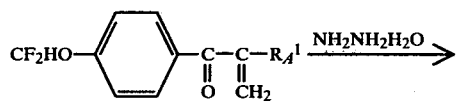

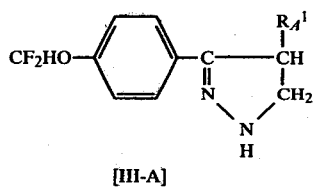

[III-A]

wherein $R_A{}^1$ represents phenyl group or halogen-substituted phenyl group.

Scheme (2-B)

The compound having the formula (III) wherein $R^1$ represents hydrogen atom or a lower alkyl group; $R^2$ represents hydrogen atom.

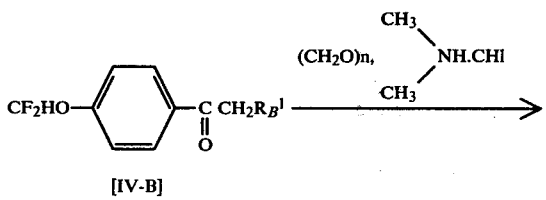

[IV-B]

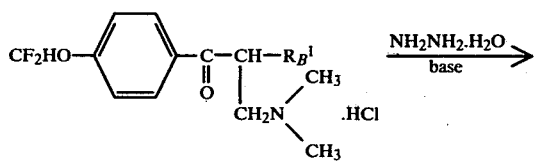

[III-B]

wherein $R_B{}^1$ represents hydrogen atom or a lower alkyl group.

Scheme (2-C)

The compounds having the formula (III) wherein $R^2$ represents phenyl group or a halogen-substituted phenyl group.

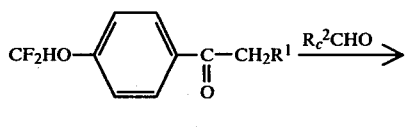

[IV]

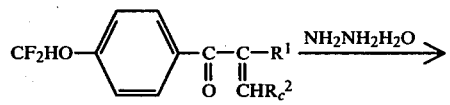

[III-C]

wherein $R^1$ represents hydrogen atom, a lower alkyl group, phenyl group or a halogen-substituted phenyl group; and $R_c{}^2$ represents phenyl group or halogen-substituted phenyl group.

The 4-difluoromethoxy acyl benzene having the formula (IV) is produced by reacting 4-hydroxy acyl benzene having the formula (V) with difluorocarbene.

The 3-(4-difluoromethoxyphenyl)-2-pyrazoline derivatives having the formula (III) can be produced by selecting from the schemes (2-A), (2-B) and (2-C) depending upon the substituent groups of $R^1$ and $R^2$ in the formula (III).

In the scheme (2-A), the 2-pyrazoline derivative having the formula (III-A) is produced by reacting formaldehyde in an acidic medium in the presence of a solvent and a catalyst and reacting the product with hydrazine in a solvent such as an alcohol such as ethanol and propanol.

In the scheme (2-B), the dimethyl aminomethylated product is produced by reacting dimethylamine hydrochloride with paraformaldehyde in a solvent such as ethanol in the presence of an acid catalyst such as conc. hydrochloric acid and then, hydrazine is added to the product in a solvent such as methanol in the presence of a base such as 50% NaOH aqueous solution and the mixture is heated to obtain 2-pyrazoline derivative having the formula (III-B).

In the scheme (2-C), the 2-pyrazoline derivative having the formula (III-C) is produced by reacting an aldehyde derivative in a solvent such as an alcohol such as ethanol in the presence of a base such as NaOH aqueous solution and then reacting the resulting chalcone derivative with hydrazine in an alcohol such as ethanol while heating.

The 2-pyrazoline derivatives having the formula (III) produced by these reactions can be isolated and purified. In many cases, however, these products are unstable to decompose by maintaining at room temperature. Thus, certain products should be maintained in nitrogen atmosphere at a low temperature. In a practical operation, the pyrazoline derivative having the formula (I) of the present invention can be produced without an isolation and purification of the 2-pyrazoline derivative (III) by reacting the product with a phenyl isocyanate derivative or a phenyl isothiocyanate derivative.

The typical pyrazoline derivatives of the present invention will be described in Tables 1 and 2.

TABLE 1

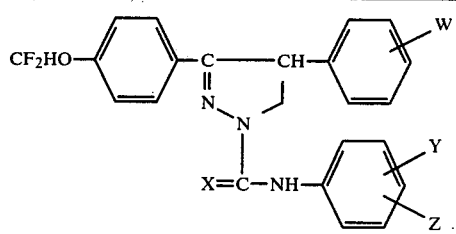

| No. | W | X | Y.Z | Melting point (°C.) |
|---|---|---|---|---|
| 1 | H | O | H | 150–152 |
| 2 | H | O | 2-F | |
| 3 | H | O | 3-F | |
| 4 | H | O | 4-F | 163–165 |
| 5 | H | O | 2-Cl | 180–182 |
| 6 | H | O | 3-Cl | 130–132 |
| 7 | H | O | 4-Cl | 147–148 |
| 8 | H | O | 3-Br | |
| 9 | H | O | 4-Br | 148–152 |
| 10 | H | O | 4-I | 149.5–151.5 |
| 11 | H | O | 2,4-$F_2$ | |
| 12 | H | O | 2-F, 4-Cl | 135–139 |
| 13 | H | O | 3-Cl, 4-F | 133–134.5 |
| 14 | H | O | 2,4-$Cl_2$ | 144–147 |
| 15 | H | O | 2,5-$Cl_2$ | |
| 16 | H | O | 3,4-$Cl_2$ | 126–128 |
| 17 | H | O | 3,5-$Cl_2$ | 170–173 |
| 18 | H | O | 2,4-$Br_2$ | |
| 19 | H | O | 2-Cl, 6-$CH_3$ | |
| 20 | H | O | 2-$CH_3$, 3-Cl | 158.5–160 |
| 21 | H | O | 2-$CH_3$, 4-Cl | 154–158 |
| 22 | H | O | 3-Cl, 4-$CH_3$ | 103–120 |
| 23 | H | O | 2-$CH_3$, 4-Br | |
| 24 | H | O | 3-$CH_3$ | |
| 25 | H | O | 4-$CH_3$ | 145–147 |
| 26 | H | O | 2-$C_2H_5$ | |
| 27 | H | O | 4-$C_2H_5$ | |
| 28 | H | O | 4-$CH(CH_3)_2$ | 138.5–141 |
| 29 | H | O | 4-n-$C_4H_9$ | |
| 30 | H | O | 3,4-$(CH_3)_2$ | |
| 31 | H | O | 3,5-$(CH_3)_2$ | |
| 32 | H | O | 2-$CH_3$, 6-$C_2H_5$ | |
| 33 | H | O | 2,6-$(C_2H_5)_2$ | |
| 34 | H | O | 2-$OCH_3$, 4-Cl | |
| 35 | H | O | 2-$OCH_3$, 5-Cl | |
| 36 | H | O | 2-$CH_3$, 4-$OCH_3$ | |
| 37 | H | O | 2-$OCH_3$ | |
| 38 | H | O | 4-$OCH_3$ | 142–146 |
| 39 | H | O | 4-$OC_2H_5$ | |
| 40 | H | O | 4-O—n$C_4H_9$ | 143–145 |
| 41 | H | O | 2,4-$(OCH_3)_2$ | |
| 42 | H | O | 3,5-$(OCH_3)_2$ | |
| 43 | H | O | 3-$NO_2$ | |
| 44 | H | O | 4-$NO_2$ | 188–193 |
| 45 | H | O | 2-$NO_2$, 4-Cl | |
| 46 | H | O | 3-$NO_2$, 4-F | |
| 47 | H | O | 3-$NO_2$, 4-$CH_3$ | |
| 48 | H | O | 2-$CH_3$, 4-$NO_2$ | |
| 49 | H | O | 2-F, 5-$NO_2$ | |
| 50 | H | O | 2-$CH_3$, 5-$NO_2$ | |
| 51 | H | O | 2-$OCH_3$, 5-$NO_2$ | |
| 52 | H | O | 2-$CF_3$ | |
| 53 | H | O | 3-$CF_3$ | 120–122 |
| 54 | H | O | 4-$CF_3$ | 163–165 |
| 55 | H | O | 2-$CF_3$, 4-Br | |
| 56 | H | O | 3-$CF_3$, 4-Cl | 137–140 |
| 57 | H | O | 3,5-$(CF_3)_2$ | |
| 58 | H | O | 3-CN | |

TABLE 1-continued

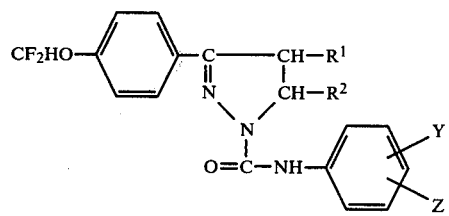

| No. | W | X | Y.Z | Melting point (°C.) |
|---|---|---|---|---|
| 59 | H | O | 4-CN | 169–172 |
| 60 | H | O | 3-$SCH_3$ | |
| 61 | H | O | 4-$SCH_3$ | 158.5–160.5 |
| 62 | H | O | 4-$CH_3CO$ | 196–200 |
| 63 | H | S | H | |
| 64 | H | S | 4-Cl | 158–161 |
| 65 | H | S | 4-$CF_3$ | |
| 66 | H | S | 4-$NO_2$ | |
| 67 | Cl | O | 4-Cl | 124–128 |
| 68 | Cl | O | 4-Br | 132–136 |
| 69 | Cl | O | 4-$CF_3$ | 143–147 |
| 70 | F | O | 4-Cl | 130–133 |
| 71 | F | O | 4-Br | 135–139 |
| 72 | F | O | 4-$CF_3$ | 158–162 |
| 73 | F | O | 2-F, 4-Cl | |
| 74 | F | O | 3,4-$Cl_2$ | 139.5–142 |
| 75 | F | O | 4-$CH_3$ | 112–114 |
| 76 | F | O | 4-$OCH_3$ | 114–119 |
| 77 | F | O | 4-$NO_2$ | 174–178 |

TABLE 2

$$CF_2HO-\text{Ar}-\underset{N\diagdown N}{\overset{C}{\|}}\underset{CH-R^2}{\overset{CH-R^1}{|}}$$
$$O=C-NH-\text{Ar}(Y,Z)$$

| No. | $R^1$ | $R^2$ | Y.Z | Melting point (°C.) |
|---|---|---|---|---|
| 78 | H | H | 3-Cl | 116–119 |
| 79 | H | H | 4-Cl | 137–140 |
| 80 | H | H | 4-Br | 131–134 |
| 81 | H | H | 2-F, 4-Cl | 135–136 |
| 82 | H | H | 3,4-$Cl_2$ | 148–150 |
| 83 | H | H | 4-$CH_3$ | 122–126 |
| 84 | H | H | 4-$OCH_3$ | 110–112 |
| 85 | H | H | 3-$CF_3$ | 120–122 |
| 86 | H | H | 4-CN | 149–154 |
| 87 | $CH_3$ | H | 4-Cl | 96–98 |
| 88 | $CH_3$ | H | 4-Br | 67–69 |
| 89 | $CH_3$ | H | 4-$CF_3$ | 105–108 |
| 90 | H |  | 4-Cl | 137–140 |
| 91 | H |  | 4-Br | 145–147 |
| 92 | H |  | 4-$NO_2$ | 157–158 |

TABLE 2-continued

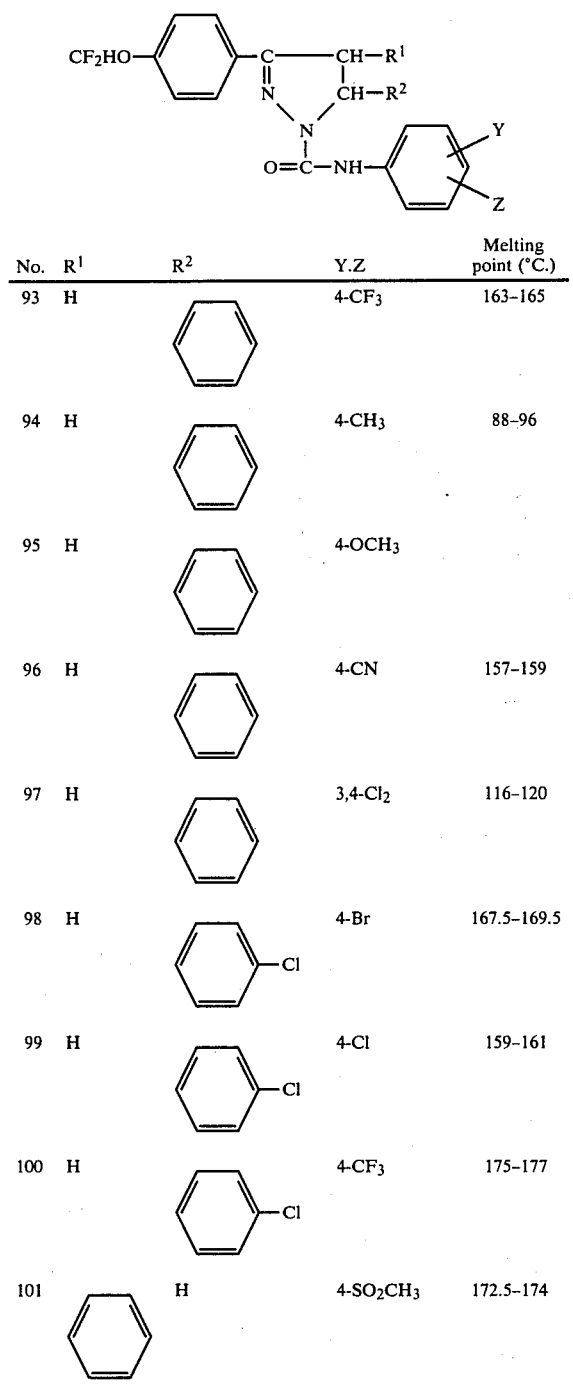

| No. | R¹ | R² | Y.Z | Melting point (°C.) |
|---|---|---|---|---|
| 93 | H | phenyl | 4-CF$_3$ | 163–165 |
| 94 | H | phenyl | 4-CH$_3$ | 88–96 |
| 95 | H | phenyl | 4-OCH$_3$ | |
| 96 | H | phenyl | 4-CN | 157–159 |
| 97 | H | phenyl | 3,4-Cl$_2$ | 116–120 |
| 98 | H | 4-Cl-phenyl | 4-Br | 167.5–169.5 |
| 99 | H | 4-Cl-phenyl | 4-Cl | 159–161 |
| 100 | H | 4-Cl-phenyl | 4-CF$_3$ | 175–177 |
| 101 | phenyl | H | 4-SO$_2$CH$_3$ | 172.5–174 |

Certain compounds of the present invention include geometrical isomers and optical isomers having asymmetric carbon atom at 4- or 5-position of 2-pyrazoline ring. These isomers are also included in the compounds of the present invention.

The serial numbers of the compounds described in Tables 1 and 2 are referred in the following Preparations, Compositions and Tests.

The compounds of the present invention are useful as insect pesticides for controlling insect pests in sanitation, and various insect pests in agriculture and horticulture which cause damages to rice, vegetable, fruits, cotton, and other crop plants and flowers and insect pests in forest and insect pests in storages.

The typical insect pests which are controlled by the compounds of the pest invention are provided for purposes of illustration only.

Orthoptera
German Cockroach (Blattella germanica)
Rice Grasshopper (OXya yezoensis)
Thysanoptera
Rice Thrips (Baliothrips biformis)
Hemiptera
Rice Stink Bug (Lagynotomus elongatus)
Green Stink Bug (Nezcra antennata)
Rice Bug (Leptocorisa chinensis)
Bean Bug (Riotortus clavatus)
Cotton Bug (Dysdercus cingulatus)
Gvape Leafhopper (Epiacanthus stramineus)
Green Rice Leafhopper (Nephotettix cincticeps)
Small Brown Planthopper (Laodelphax striatellus)
Brown Rice Planthopper (Nilaparvata lugens)
White-backed Rice Planthopper (Sogatella furcifera)
Citrus Psylla (Diaphorina citri)
Greenhouse Whitefly (Trialeurodes vaporariorum)
Cowpea Aphid (Aphis craccivora)
Cotton Aphid (Aphis gossypii)
Apple Aphid (Aphis spiraecola)
Green Peach Aphid (Myzue persicae)
Citrus Mealybug (Planococcus citri)
Comstock Mealybug (Pseudcoccus censtocki)
Red Scale (Aonidiella aurantri)
San Jose Scale (Comstockaspis perniciosa)
Arrowhead Scale (Unaspis yanonensis)
Lepidoptera
Apple Leafminer (Phyllonorycfer ringoneella)
Citrus Leafminer (Phyllocnistis citrella)
Diamondback Moth (Plutella xylostella)
Pink Bollworm (Pectinophora gossypiella)
Potato Tuberworm (Phthorimaea operculella)
Peach Fruit Moth (Carposina niponensis)
Summer Fruit Tortrix (Adoxophyes orana)
Oriental Fruit Moth (Grapholita molesta)
Soybean Pod Borer (Leguminivora glycinivorella)
Rice Stem Borer (Chilo suppressalis)
Rice Leafroller (Chaphalocrocis medinalis)
Pea Pod Borer (Etiella zinckenella)
Oriental Corn Borer (Ostrinia furnacalis)
Yellow Rice Borer (Tryporyza incertulas)
Cutworm (Agrotis segetum)
Cotton Looper (Anomis flava)
American Bollworm, Cotton Bollworm or Tobacco Budworm (Heliothis armigera, H. zeae H. virescens)
Cabbage armyworm (Mamestra brassicae)
Beet Semi Looper (Plusia nigrisigna)
Rice Armyworm (Pseudaletia separata)
Pink Borer (Sesamia inferens)
Common Cutworm (Spodoptera litura)
Common White (Pieris rapae crucivora)
Smaller Citrus Dog (Papilio xuthus)
Rice Skipper (Parnara guttata)
Codling Moth (Cydia pomonella)
Coleoptera
Cupreous Chafer (Anomala cuprea)
Asiatic Garden Beetle (Maladera castanea)
Japanese Beetle (Popillia Japonica)
Twenty-eight-spotted Ladybeetle (Henosepilachna vigintioctopunctata)
Curcurbit Leaf Beetle (Aulacophora femoralis)
Rice Leaf Beetle (Oulema oryzae)
Striped Flea Beetle (Phyllotreta striolata)
Rice Plant Weevil (Echinocnemus squameus)
Ricewater Weevil (Lissorhoptrus oryzophilus)
Vegetable Weevil (Listroderes obliquus)
Maize Weevil (Sitophilus zeamais)
Bull Weevil (Anthonomus grandis)
Corn Rootworms (Diabrotica spp.)
Colorado Potato Beetle (Leptinotarsa decemlineata)
Hymenoptera

| | |
|---|---|
| Fire Ant | (*Solenopsis geminata*) |
| Diptera | |
| Soybean Pud Gall Midge | (*Asphondylia* spp.) |
| Oriental Fruit Fly | (*Dacus dorsalis*) |
| Rice Leafminer | (*Hydrellia griseola*) |
| Rice Stem Maggot | (*Chlorops oryzae*) |
| Rice Leafminer | (*Agromyza oryzae*) |
| Seedcorn Maggot | (*Hylemya platura*) |
| Mediterranean Fruit Fly | (*Ceratitis capitata*) |
| Rice Gall Midge | (*Orseolia oryzae*) |
| House Fly | (*Musca domestica*) |
| Pale House Mosquito | (*Culex pipiens pallens*) |

The insecticidal activity of the compounds of the present invention is imparted not only young larva but also old larva in direct or in penetration by direct contact or immersion. The compounds of the present invention are also effective to control various acarina and nematode.

In the application of the insect pesticidal composition of the present invention, it is preferable to apply it at a concentration of 0.01 to 10,000 ppm preferably 0.1 to 2,000 ppm of the active ingredient. In order to control aquatic insect pests, the composition having said concentration can be sprayed to the part to control the aquatic insect pests. Therefore, the concentration of the active ingredient in water can be lower.

In the application of the compound of the present invention as the insect pesticide, it is preferable to prepare a composition by mixing the active ingredient with a desired solid carrier such as clay, talc and bentonite; or a liquid carrier such as water, alcohols (methanol, ethanol etc.), ketones, ethers, aliphatic hydrocarbons, aromatic hydrocarbons (benzene, toluene, xylene etc.), esters and nitriles, if necessary, with an emulsifier, a dispersing agent, a suspending agent, a spreader, a penetrant and a stabilizer so as to form suitable compositions for practical applications in the form of an emulsifiable concentrate, an oil spray, a wettable powder, a dust, a granule, a tablet, a paste a floable, a bait poison, an aerosol, a fumigrant, a mosquito-repellent incense and an electric mosquito-repellent incense.

It is possible to blend the active ingredient of the present invention to a suitable other active ingredient such as the other insect pesticides, germicides, herbicides, plant growth regulators, and fertilizers in the preparation of the composition or in the application.

The present invention will be further illustrated by certain examples of Preparations, Compositions and Tests which are provided for purposes of illustration only and are not intended to be limiting the present invention.

Preparation 1

1-(4-Chlorophenylcarbamoyl)-3-(4-difluoromethoxyphenyl)-4-phenyl-2-pyrazoline (Compound No. 7)

(a) Preparation of 3-(4-difluoromethoxyphenyl)-4-phenyl-2-pyrazoline (Intermediate)

A mixture of 17 g. of 4'-hydroxy-2-phenylacetophenone and 30 g. of sodium hydroxide in 40 ml. of water and 50 ml. of dioxane was heated at 70° to 80° C. and 22 g. of Freon 22 gas was fed into the solution during 1 hour while heating. After cooling the reaction mixture, 150 ml. of water and 150 ml. of ethyl ether were added to the reaction mixture and an organic phase was obtained by an extraction. The organic phase was separated and dried over anhydrous sodium sulfate and ethyl ether was distilled off to obtain 17.6 g. of 4'-difluoromethoxy-2-phenylacetophenone (melting point of 39.0°–40.0° C.). Into a mixture of 0.9 ml. of pyridine, 0.9 ml. of acetic acid, 25 ml. of 37% formaline and 180 ml. of methanol, 17.5 g. of the resulting compound was added and the mixture was refluxed for 3 hours to react them. The reaction was concentrated under a reduced pressure and 150 ml. of water and 200 ml. of chloroform were added. The resulting organic phase was separated and dried over anhydrous sodium sulfate and chloroform was distilled off to obtain 18.0 g. of 4'-difluoromethoxy-2-phenylacrylophenone ($N_D^{20}$ 1.5819). A mixture of 17.5 g. of the product, 8 ml. of hydrazine hydrate and 150 ml. of ethanol was refluxed for 3 hours to react them. After the reaction, the reaction mixture was concentrated under a reduced pressure and 80 ml. of water and 100 ml. of chloroform were added. The resulting organic phase was separated and dried over anhydrous sodium sulfate and chloroform was distilled off to obtain 17.5 g. of 3-(4-difluoromethoxyphenyl)-4-phenyl-2-pyrazoline (melting point of 65°–75° C.).

(b) Preparation of Compound No. 7

A mixture of 5.8 g. of 3-(4-difluoromethoxyphenyl)-4-phenyl-2-pyrazoline obtained in the step (a) and 3.1 g. of 4-chlorophenyl isocyanate in 200 ml. anhydrous ethyl ether was refluxed for 6 hours to react them. After cooling, the precipitated crystal (5.3 g.) was separated by a filtration.

It was confirmed that the product was 1-(4-chlorophenylcarbamoyl)-3-(4-difluoromethoxyphenyl)-4-phenyl-2-pyrazoline (melting point of 147.0°–148.0° C.) by the NMR spectrum.

Preparation 2

1-(3,4-Dichlorophenylcarbamoyl)-3-(4-difluoromethoxyphenyl)-4-phenyl-2-pyrazoline (Compound No. 16)

A mixture of 5.8 g. of 3-(4-difluoromethoxyphenyl)-4-phenyl-2-pyrazoline obtained in the step (a) of Preparation 1, and 3.8 g. of 3,4-dichlorophenyl isocyanate in 200 ml. of anhydrous ethyl ether was refluxed for 6 hours to react them. After cooling the reaction mixture, the precipitated crystal (5.3 g.) was separated by a filtration. It was confirmed that the product was 1-(3,4-dichlorophenylcarbamoyl)-3-(4-difluoromethoxyphenyl)-4-phenyl-2-pyrazoline (melting point of 126.0°–128.0° C.) by the NMR spectrum.

Preparation 3

1-(4-Chlorophenylthiocarbamoyl)-3-(4-difluoromethoxyphenyl)-4-phenyl-2-pyrazoline (Compound No. 64)

A mixture of 5.8 g. of 3-(4-difluoromethoxyphenyl)-4-phenyl-2-pyrazoline and 3.4 g. of 4-chlorophenylisothiocyanate in 200 ml. of anhydrous ethyl ether was refluxed for 6 hours to react them. After cooling the reaction mixture, the precipitated crystal (6.1 g.) was separated by a filtration. It was confirmed that the product was 1-(4-chlorophenylthiocarbamoyl)-3-(4-difluoromethoxyphenyl)-4-phenyl-2-pyrazoline (melting point of 158.0°–161.0° C.) by the NMR spectrum.

Preparation 4

1-(4-Trifluoromethylphenylcarbamoyl)-3-(4-difluoromethoxyphenyl)-4-(4-chlorophenyl)-2-pyrazoline (Compound No. 69)

(a) Preparation of 3-(4-difluoromethoxyphenyl)-4-(4-chlorophenyl-2-pyrazoline (Intermediate)

In accordance with the process of the step (a) of Preparation 1, 4'-difluoromethoxy-2-(4-chlorophenyl)-acetophenone (melting point of 74.0°–76.0° C.) was produced as an intermediate by using 20 g. of 4'-hydroxy-2-(4-chlorophenyl)-acetophenone instead of 4'-hydroxy-2-phenylacetophenone. Then, 4'-difluoromethoxy-2-(4-chlorophenyl) acrylophenone ($N_D^{20.5}$ 1.5752) was obtained by reacting the intermediate with formaline. Then, a reaction of hydrazine hydrate with the product was carried out to obtain 11.6 g. of 3-(4-difluoromethoxyphenyl)-4-(4-chlorophenyl)-2-pyrazoline. The product was used as the intermediate for the next step without a purification.

(b) Preparation of Compound No. 69

Into 150 ml. of anhydrous ethyl ether, 6.5 g. of 3-(4-difluoromethoxyphenyl)-4-(4-chlorophenyl)-2-pyrazoline obtained in the step (a) and 3.7 g. of 4-trifluoromethylphenylisocyanate were added and the mixture was kept at room temperature for one night and the precipitated crystal (6.5 g.) was separated by a filtration. It was confirmed that the product was 1-(4-trifluoromethylphenyl)-3-(4-difluoromethoxyphenyl)-4-(4-chlorophenyl)-2-pyrazoline (melting point of 143.0°–147.0° C.) by the NMR spectrum.

Preparation 5

1-(4-Methoxyphenylcarbamoyl)-3-(4-difluoromethoxyphenyl)-2-pyrazoline (Compound No. 84)

(a) Preparation of 3-(4-difluoromethoxyphenyl)-2-pyrazoline (Intermediate)

In a reactor A, 54.4 g. of 4-hydroxyacetophenone was added to a solution of 17 g. of sodium hydroxide in 160 ml. of water and 400 ml. of dioxane.

On the other hand, in a reactor B, a solution of 80 g. of sodium hydroxide in 300 ml. of water and 360 ml. of dioxane was prepared. The reactor B was heated to 80° C. and Freon 22 gas was fed and the resulting difluorocarbene was fed through a polytetrafluoroethylene tube into the reactor A at room temperature. After feeding 200 g. of Freon 22 gas, the reactor A was cooled and 400 ml. of water and 500 ml. of ethyl ether were charged for an extraction. The resulting organic phase was separated and dried over anhydrous sodium sulfate and ethyl ether was distilled off to obtain a crude product. The crude product was distilled under a reduced pressure to obtain 44.6 g. of 4-difluoromethoxyacetophenone having a boiling point of 98°–100° C./3 mmHg. A mixture of 44 g. of the resulting product, 19.3 g. of dimethylamine hydrochloride, 7.3 g. of paraformaldehyde and 30 ml. of ethanol and 3 ml. of conc. hydrochloric acid was refluxed for 3 hours to react them. The solvent was distilled off under a reduced pressure and the crystal as the residue was obtained. The residue was mixed with 18 ml. of acetone and the crystal was separated by a filtration to obtain 4'-difluoromethoxy-3-dimethylaminopropiophenone hydrochloride having a melting point of 135.0°–140.0° C.

A mixture of the resulting crystal 150 ml. of methanol, 33 ml. of hydrazine hydrate, 17 ml. of 50% NaOH aq. sol. and 45 ml. of water was refluxed for 1 hour. Methanol was distilled off and then, dichloromethane and water were added for an extraction. The resulting organic phase was separated and dried over anhydrous sodium sulfate and dichloromethane was distilled off to obtain 32 g. of 3-(4-difluoromethoxyphenyl)-2-pyrazoline. The product was used as the intermediate in the next reaction step without any purification.

(b) Preparation of Compound No. 84

Into 150 ml. of anhydrous ethyl ether, 4.2 g. of 3-(4-difluoromethoxyphenyl)-2-pyrazoline obtained in the step (a) and 3.0 g. of 4-methoxyphenylisocyanate were charged and the mixture was kept at room temperature for one night and the precipitated crystal (5.2 g.) was separated by a filtration.

It was confirmed that the product was 1-(4-methoxyphenylcarbamoyl)-3-(4-difluoromethoxyphenyl)-2-pyrazoline (melting point of 110.0°–112.0° C.) by the NMR spectrum.

Preparation 6

1-(4-Chlorophenylcarbamoyl)-3-(4-difluoromethoxyphenyl)-4-methyl-2-pyrazoline (Compound No. 87)

(a) Preparation of 3-(4-difluoromethoxyphenyl)-4-methyl-2-pyrazoline (Intermediate)

In accordance with the process of Preparation 5, 4-difluoromethoxy propiophenone (boiling point of 108°–109° C./3 mmHg) was produced as an intermediate by using 60 g. of 4-hydroxypropiophenone instead of 4-hydroxyacetophenone. Then, the product was dimethylaminomethylated to obtain 4'-difluoromethoxy-3-dimethylamino-2-methylpropiophenone hydrochloride (melting point of 134.0°–136.0° C.) Then, a reaction of hydrazine hydrate with the product in the presence of 50% NaOH aq. sol. was carried out to obtain 37 g. of 3-(4-difluoromethoxyphenyl)-4-methyl-2-pyrazoline. The product was used as the intermediate for the next step without a purification.

(b) Preparation of Compound No. 87

Into 150 ml. of anhydrous ethyl ether, 4.7 g. of 3-(4-difluoromethoxyphenyl)-4-methyl-2-pyrazoline obtained in the step (a) and 3.1 g. of 4-chlorophenylisocyanate were added and the mixture was kept at room temperature for one night and then ethyl ether was distilled off under a reduced pressure to obtain a crude product. The crude product was purified by a silica gel thin layer chromatography (developing solvent:benzene:ethyl acetate=5:1) to obtain 3.1 g. of the product in the crystalline form.

It was confirmed that the product was 1-(4-chlorophenylcarbamoyl)-3-(4-difluoromethoxyphenyl)-4-methyl-2-pyrazoline (melting point of 96.0°–98.0° C.) by the NMR spectrum.

Preparation 7

1-(4-Bromophenylcarbamoyl)-3-(4-difluoromethoxyphenyl)-5-(4-chlorophenyl)-2-pyrazoline (Compound No. 98)

(a) Preparation of 3-(4-difluoromethoxyphenyl)-5-(4-chlorophenyl)-2-pyrazoline (Intermediate)

Into 10 ml. of ethanol and 20 ml. of 10% NaOH aqueous solution, 5.6 g. of 4'-difluoromethoxyacetophenone obtained as the intermediate in the step (a) of Preparation 5 was added and then 4.2 g. of p-chlorobenzaldehyde was added to the mixture at room temperature while stirring and the mixture was stirred for 1 hour. The crystal was precipitated. The mixture was cooled to 0° C. and kept at 0° C. for 1 hour. The precipitated crystal was separated by a filtration and washed twice with 20 ml. of water and once with 20 ml. cold ethanol and dried under a reduced pressure for 3 hours to obtain 8.4 g. of 4-chloro-4'-difluoromethoxy chalcone (melting point of 114°–115° C.).

A mixture of 8.4 g. of the product in 6 ml. of hydrazine hydrate and 80 ml. of ethanol was refluxed for 2 hours while heating. After the reaction, the reaction mixture was concentrated under a reduced pressure and then, 50 ml. of water and 80 ml. of chloroform were added. The organic phase was separated and dried over anhydrous sodium sulfate and chloroform was distilled off to obtain 8.8 g. of 3-(4-difluoromethoxyphenyl)-5-(4-chlorophenyl)-2-pyrazoline.

(b) Preparation of Compound No. 98

Into 20 ml. of anhydrous ethyl ether, 1 g. of 3-(4-difluoromethoxyphenyl)-5-(4-chlorophenyl)-2-pyrazoline obtained in the step (a) and 0.5 g. of 4-bromophenylisocyanate were charged to react them at room temperature for 15 hours. The precipitated crystal was separated by a filtration.

It was confirmed that the product was 1-(4-bromophenylcarbamoyl)-3-(difluoromethoxyphenyl)-5-(4-chlorophenyl)-2-pyrazoline (melting point of 167.5°–169.5° C.) by the NMR spectrum.

Certain examples of the compositions of the compounds of the present invention as insect pesticides are provided for purposes of illustration only and are not intended to be limiting the present invention.

Composition 1: Emulsifiable concentrate

| Active ingredient: | 10 wt. parts |
|---|---|
| Xylene: | 80 wt. parts |
| Sorpol 2680 (Toho Chem.): | 10 wt. parts |

The components were uniformly mixed to prepare an emulsifiable concentrate. The emulsifiable concentrate was diluted with water to 50–100,000 times and it was sprayed in amounts of 10–500 liter/10 ares.

As the active ingredient, Compound No. 1, 4, 6, 7, 9, 12, 16, 20, 25, 28, 38, 40, 44, 53, 54, 59, 61, 64, 67, 68, 69, 70, 71, 72, 75, 77 and 78–100 were used.

Composition 2: Oil solution

| Active ingredient: | 50 wt. parts |
|---|---|
| Methyl cellosolve: | 50 wt. parts |

The components were uniformly mixed to obtain an oily solution.

The oil solution was applied in amounts of 0.1 to 50 ml./m² to a drain or puddle or in amounts of 10–100 ml./10 ares by airplane spray. As the active ingredient, Compound No. 10 and the other compounds in Tables were used.

Composition 3: Wettable powder

| Active ingredient: | 25 wt. parts |
|---|---|
| Zeeklite PFP: | 65 wt. parts |
| Carplex #80: | 2 wt. parts |
| Sorpol 5050: | 2 wt. parts |
| Sodium ligninesulfonate: | 6 wt. parts |

The components were uniformly ground and mixed to obtain a wettable powder. The wettable powder was diluted with 100 to 250,000 times of water and it was sprayed in amounts of 20 to 500 liter/10 ares.

As the active ingredient, Composition No. 67 and other compounds in Tables were used.

Composition 4: Dust

| Active ingredient: | 3.0 wt. parts |
|---|---|
| Carplex #80: | 0.5 wt. parts |
| Clay: | 95 wt. parts |
| Diisopropyl phosphate: | 1.5 wt. parts |

The components were uniformly mixed to obtain a dust. The dust was applied in amounts of 0.03 to 15 kg/10 ares.

As the active ingredient, Composition No. 9 and other compounds in Tables were used.

Composition 5: Bait Poison

| Wheat bran: | 52 wt. parts |
|---|---|
| Rice bran: | 15 wt. parts |
| Wheat powder: | 30 wt. parts |
| Raw sugar (muscovado): | 3 wt. parts |

The components were uniformly mixed and each active ingredient was added at a ratio of 0.2% base on the total components. Water was added at a ratio of 50% based on the total components and the mixture was granulated by a pelleter and dried at 50° to 60° C. by hot air. The resulting bait poison was placed in amounts of 0.1–5 g./m² around a root of a plant.

As the active ingredient, Compound No. 1, 4, 7, 9, 10, 16, 21, 25, 28, 38, 40, 44, 53, 54, 56, 59, 61, 62, 64 and 67–100 were used.

The insect pesticidal activities of the compounds of the present invention will be illustrated by tests.

EXPERIMENT 1

Contact test for killing adult houseflies

A 1 ml. of 100 ppm solution of each active ingredient of the present invention in acetone was dropped onto the bottom of a Petri dish (9 cm) and was spread uniformly over the surface of the dish. Acetone was completely evaporated at room temperature Ten adult houseflies were placed in the dish, which was covered with a plastic cover having many holes. The Petri dish was maintained in a constant temperature room at 25° C. for 48 hours and each percent mortality of the houseflies was determined. The test was repeated twice and the results are shown in Table 3.

TABLE 3

| Active ingredient | Percent mortality (%) |
|---|---|
| Compound No. 7 | 100 |
| No. 9 | 100 |
| No. 12 | 95 |
| No. 16 | 100 |
| No. 44 | 100 |
| No. 53 | 100 |
| No. 54 | 100 |
| No. 64 | 100 |
| No. 67 | 100 |
| No. 68 | 100 |
| No. 69 | 100 |
| No. 70 | 100 |
| No. 71 | 100 |
| No. 72 | 100 |
| No. 74 | 100 |
| No. 87 | 100 |
| No. 88 | 100 |

EXPERIMENT 2

Contact test for killing green rice leafhopper

Stems and leaves of a rice seedling were dipped in each emulsion of each composition of the active ingredient of the present invention (100 ppm) for 10 seconds and were dried in air. The stems and leaves were covered with a glass cylinder adult green rice leaf-hoppers which are resistive to the conventional organic phosphorus type insect pesticides were released into the glass cylinder which was covered with a cover having holes and was maintained in a constant temperature room at 25° C. for 48 hours and each percent mortality was determined.

The results are shown in Table 4.

TABLE 4

| Active ingredient | Percent mortality (%) |
|---|---|
| Compound No. 7 | 100 |
| Compound No. 9 | 100 |
| Compound No. 16 | 100 |
| Compound No. 44 | 100 |
| Compound No. 54 | 100 |
| Reference Comp. A | 20 |

Note:
Reference Compound A:

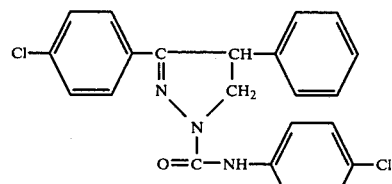

(Japanese Unexamined Patent Publication No. 41358/1976)

EXPERIMENT 3

Contact test for killing Common cutworm

Leaves of cabbage were dipped in aqueous emulsion of each active ingredient of the compounds of the invention or the reference for 10 seconds. The leaves were taken up and dried in air and put in a Petri dish. Common cutworms (second instar) were put in the Petri dish which was covered with a cover having many holes. The Petri dish was maintained in a constant temperature room at 25° C. for 48 hours and each percent mortality was determined. The results are shown in Table 5.

TABLE 5-1

| Active ingredient | Concentration (ppm) | Percent mortality (%) |
|---|---|---|
| Compound No. 7 | 1.25 | 100 |
| No. 9 | 1.25 | 100 |
| No. 10 | 1.25 | 100 |
| No. 16 | 1.25 | 100 |
| No. 21 | 1.25 | 100 |
| No. 54 | 1.25 | 100 |
| No. 59 | 1.25 | 100 |
| No. 64 | 1.25 | 100 |
| No. 67 | 1.25 | 100 |
| No. 68 | 1.25 | 100 |
| No. 69 | 1.25 | 100 |
| No. 70 | 1.25 | 100 |
| No. 71 | 1.25 | 100 |
| No. 72 | 1.25 | 100 |
| No. 74 | 1.25 | 100 |
| No. 76 | 1.25 | 100 |
| No. 77 | 1.25 | 100 |
| Reference Comp. A | 1.25 | 70 |

TABLE 5-2

| Active ingredient | Concentration (ppm) | Percent mortality (%) |
|---|---|---|
| Compound No. 79 | 10 | 100 |
| No. 87 | 10 | 100 |
| No. 88 | 10 | 100 |
| No. 89 | 10 | 100 |
| No. 90 | 10 | 100 |
| No. 93 | 10 | 100 |
| No. 98 | 10 | 100 |
| No. 99 | 10 | 100 |
| No. 100 | 10 | 100 |
| Reference Comp. B | 10 | 40 |
| C | 10 | 70 |
| D | 10 | 60 |

Reference Compound A

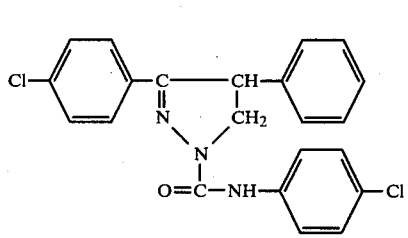

(Japanese Unexamined Patent Publication No. 41358/1976)

Reference Compound B

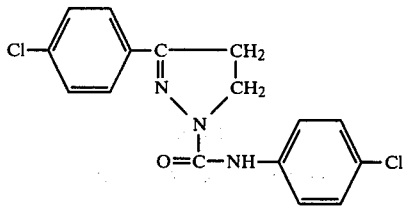

(Japanese Unexamined Patent Publication No. 87028/1973)

Reference Compound C

-continued

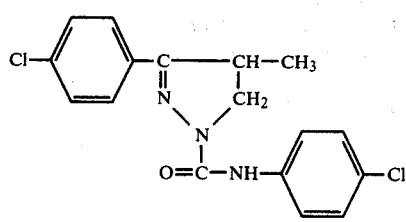

(Japanese Unexamined Patent Publication No. 41358/1976)

Reference Compound D

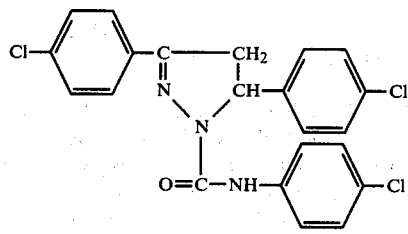

(Japanese Unexamined Patent Publication No. 87028/1973)

EXPERIMENT 4

Contact test for killing Twenty-eight-spotted Ladybeetle

Leaves of tomato were dipped in 1 ppm aqueous emulsion of each active ingredient of the compounds of the present invention and the reference for 10 seconds. The leaves were taken up and dried in air and put in a Petri dish. Ten of Twenty-eight-spotted Ladybeetles (second instar) were put in the Petri dish which was covered with a cover. The Petri dish was maintained in a constant temperature room at 25° C. for 48 hours and percent mortality was determined. The tests were carried out in two groups. The results are shown in Table 6.

TABLE 6

| Active ingredient | Percent mortality (%) |
| --- | --- |
| Compound No. 7 | 100 |
| No. 9 | 100 |
| No. 16 | 100 |
| No. 44 | 100 |
| No. 54 | 100 |
| No. 59 | 100 |
| No. 67 | 100 |
| No. 68 | 100 |
| No. 69 | 100 |
| No. 70 | 100 |
| No. 71 | 100 |
| No. 72 | 100 |
| No. 77 | 100 |
| No. 101 | 100 |
| Reference Comp. A | 70 |

EXPERIMENT 5

Bait poison test for killing Common cutworm

Into each 1/5000 are pot, planting cabbage at 4 leaf stage, each bait poison composition 5 containing each active ingredient was put in an amount of 3 kg. or 6 kg./10 ares. Common cutworm (fifth instar) were put in the pot. The pot was maintained in a constant temperature room at 25° C. After 5 hours, the percent mortality for each of the active ingredients was 100%.

EXPERIMENT 6

Contact test for killing Common cutworms (second instar): (mixed insect pesticide)

Leaves of cabbage were dipped in aqueous emulsion of each single active ingredient or each mixture of Compound No. 7 and EPN or Fenvalerate (2:1) for 10 seconds. The leaves were taken up and dried in air and put in a Petri dish. Ten of Common cutworm (second instar) were put in a Petri dish which was covered with a cover having many holes. The Petri dish was maintained in a constant temperature room at 25° C. for 72 hours and percent mortality was determined.

$LC_{50}$ (ppm) was determined by Finny equation. A synergistic coefficient was calculated from $LC_{50}$ (ppm) by the Sun method (J. Econ. Ent. 53 5, 887–892 (1960) to evaluate the synergistic effect for insect pesticides. The results are shown in Table 7.

TABLE 7

| | $LC_{50}$ (ppm) | | |
| --- | --- | --- | --- |
| | Single Compound | Mixture of Compound 7 and other (2:1) | Synergistic coefficient |
| Compound No. 7 | 0.29 | — | — |
| EPN | 1.1 | 0.22 | 192 |
| Fenvalerate | 1.7 | 0.22 | 182 |

The remarkable synergistic effects of the combination of Compound No. 7 and EPN or Fenvalerate were found.

We claim:

1. A pyrazoline derivative having the formula

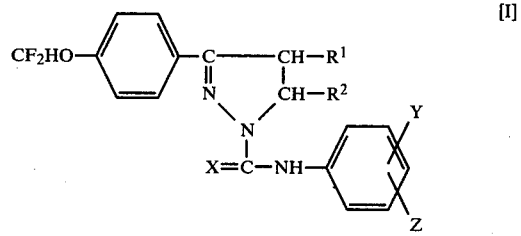

[I]

wherein $R^1$ represents hydrogen atom, a lower alkyl group, phenyl group or a halogen-substituted phenyl group; $R^2$ represents hydrogen atom or phenyl group which can have halogen substituents; X represents oxygen or sulfur atom; Y and Z respectively represent hydrogen atom, a halogen atom, a lower alkyl group, a lower alkoxy group, nitro-group, trifluoromethyl group, a lower alkylthio group, a lower alkanoyl group, nitrile group or a lower alkyl sufonyl group.

2. The pyrazoline derivative according to claim 1 having the formula (I) wherein X represents oxygen atom.

3. The pyrazoline derivative according to claim 2 having the formula (I) wherein $R^1$ represents a lower alkyl group, phenyl group, a halogen-substituted phenyl group; and $R^2$ represents hydrogen atom.

4. The pyrazoline derivative according to claim 3 having the formula (II)

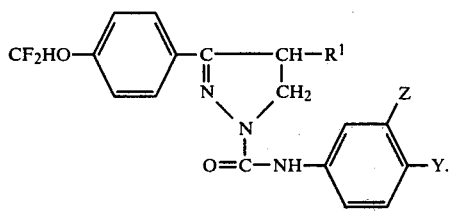

[II]

5. The pyrazoline derivative according to claim 4 having the formula (II) wherein Y represents a halogen atom, trifluoromethyl group or nitro group; Z represents hydrogen atom or a halogen atom.

6. The pyrazoline derivative according to claim 5 having the formula (II) wherein $R^1$ represents phenyl group.

7. 1-(4-Chlorophenylcarbamoyl)-3-(4-difluorometoxyphenyl)-4-phenyl-2-pyrazoline.

8. 1-(4-Bromophenylcarbamoyl)-3-(4-difluorometoxyphenyl)-4-phenyl-2-pyrazoline.

9. 1-(3,4-Dichlorophenylcarbamoyl)-3-(4-difluorometoxyphenyl)-4-phenyl-2-pyrazoline.

10. 1-(4-Nitrophenylcarbamoyl)-3-(4-difluorometoxyphenyl)-4-phenyl-2-pyrazoline.

11. 1-(4-Trifluoromethylphenylcarbamoyl)-3-(4-difluorometoxyphenyl)-4-phenyl-2-pyrazoline.

12. 1-(4-Chlorophenylcarbamoyl)-3-(4-difluorometoxyphenyl)-4-(4-fluorophenyl)-2-pyrazoline.

13. 1-(4-Bromophenylcarbamoyl)-3-(4-difluorometoxyphenyl)-4-(4-fluorophenyl)-2-pyrazoline.

14. 1-(4-Trifluoromethylphenylcarbamoyl)-3-(4-difluorometoxyphenyl)-4-(4-fluorophenyl)-2-pyrazoline.

15. 1-(3,4-Dichlorophenylcarbamoyl)-3-(4-difluorometoxyphenyl)-4-(4-fluorophenyl)-2-pyrazoline.

16. 1-(4-Nitrophenylcarbamoyl)-3-(4-difluorometoxyphenyl)-4-(4-fluorophenyl)-2-pyrazoline.

17. An insecticidal composition which comprises an effective amount of a pyrazoline derivative defined in claim 1, 2, 3, 4, 5, 6, 7, 8, 9, 10, 11, 12, 13, 14, 15 or 16 as an active ingredient and a carrier therefor.

* * * * *

UNITED STATES PATENT AND TRADEMARK OFFICE
CERTIFICATE OF CORRECTION

PATENT NO. : 4,407,813

DATED : October 4, 1983

INVENTOR(S) : Kiyomi Ozawa et al

It is certified that error appears in the above-identified patent and that said Letters Patent is hereby corrected as shown below: On the title page Please list the following two inventors in addition to Letters Patent:

--[75]   Inventors

Masayoshi Hirose   Saitama, Japan

Masaki Kudo   Saitama, Japan   --

Signed and Sealed this

Thirteenth Day of March 1984

[SEAL]

Attest:

Attesting Officer

GERALD J. MOSSINGHOFF

Commissioner of Patents and Trademarks